United States Patent
Zhang et al.

(10) Patent No.: US 11,771,628 B2
(45) Date of Patent: Oct. 3, 2023

(54) METHODS OF MAKING SILVER NANOPARTICLES AND THEIR APPLICATIONS

(71) Applicant: STELO TECHNOLOGIES, Los Gatos, CA (US)

(72) Inventors: Jingwu Zhang, San Jose, CA (US); Catherine Shachaf, Los Gatos, CA (US)

(73) Assignee: STELO TECHNOLOGIES, Los Gatos, CA (US)

( * ) Notice: Subject to any disclaimer, the term of this patent is extended or adjusted under 35 U.S.C. 154(b) by 352 days.

(21) Appl. No.: 17/106,947

(22) Filed: Nov. 30, 2020

(65) Prior Publication Data

US 2021/0161777 A1 Jun. 3, 2021

Related U.S. Application Data

(63) Continuation of application No. 16/121,310, filed on Sep. 4, 2018, now Pat. No. 10,874,595, which is a continuation of application No. 14/432,408, filed as application No. PCT/US2013/062719 on Sep. 30, 2013, now Pat. No. 10,064,793.

(60) Provisional application No. 61/744,542, filed on Sep. 28, 2012.

(51) Int. Cl.
| | |
|---|---|
| *A61K 8/19* | (2006.01) |
| *A61Q 11/00* | (2006.01) |
| *A61Q 15/00* | (2006.01) |
| *A61Q 19/10* | (2006.01) |
| *A61K 8/02* | (2006.01) |
| *A23L 33/16* | (2016.01) |
| *A61K 33/38* | (2006.01) |
| *B82Y 30/00* | (2011.01) |
| *A61L 15/28* | (2006.01) |
| *A61L 15/46* | (2006.01) |
| *A61L 15/18* | (2006.01) |
| *A61K 47/14* | (2017.01) |
| *A61K 9/10* | (2006.01) |
| *A61K 9/51* | (2006.01) |
| *A61K 8/04* | (2006.01) |
| *B22F 9/20* | (2006.01) |
| *C22B 11/00* | (2006.01) |
| *C22C 5/06* | (2006.01) |

(52) U.S. Cl.
CPC .............. *A61K 8/19* (2013.01); *A23L 33/16* (2016.08); *A61K 8/0241* (2013.01); *A61K 8/042* (2013.01); *A61K 9/10* (2013.01); *A61K 9/5123* (2013.01); *A61K 33/38* (2013.01); *A61K 47/14* (2013.01); *A61L 15/18* (2013.01); *A61L 15/28* (2013.01); *A61L 15/46* (2013.01); *A61Q 11/00* (2013.01); *A61Q 15/00* (2013.01); *A61Q 19/10* (2013.01); *B22F 9/20* (2013.01); *B82Y 30/00* (2013.01); *C22B 11/04* (2013.01); *C22C 5/06* (2013.01); *A23V 2002/00* (2013.01); *A61K 2800/28* (2013.01); *A61K 2800/412* (2013.01); *A61K 2800/621* (2013.01); *A61K 2800/624* (2013.01); *A61L 2300/104* (2013.01); *A61L 2300/404* (2013.01); *A61L 2300/624* (2013.01)

(58) Field of Classification Search
CPC . A61K 8/19; A61K 9/10; A61Q 11/00; C22C 5/06
See application file for complete search history.

(56) References Cited

U.S. PATENT DOCUMENTS

2016/0122499 A1* 5/2016 Farrugia .................. C08K 3/08
524/440

OTHER PUBLICATIONS

Wagener, P. et al. "How Citrate Ligands Affect Nanoparticle Adsorption to Microparticle Supports" Langmuir 2012, 28, 6132-6140 (Year: 2012).*

DeMelo, L.S.A. et al. "Singlet Oxygen Generation Enhanced by Silver-Pectin Nanoparticles" J. Fluoresc. 2012, 22, 1633-1638 (Year : 2012).*

* cited by examiner

*Primary Examiner* — Andrew S Rosenthal
(74) *Attorney, Agent, or Firm* — Dave Law Group LLC; Raj S. Dave

(57) ABSTRACT

Disclosed herein is a micro particle with a diameter of 10-100 microns, wherein the micro particle is coated with silver nanoparticles; and wherein the nanoparticles are coated with a polysaccharide; and wherein the polysaccharide coating is digestible by bacteria. Also, disclosed is a method of making silver nanoparticles using an ascorbic acid derivative or an alpha-hydroxyl carboxylic acid derivative as a reducing agent. The silver nanoparticles may be coated onto micro particles, embedded in hydrogel particles or coated with polysaccharide. The silver nanoparticles may be used in a wound dressing, a bandage, a fungal treatment product, a deodorant, a floss product, a toothpick, a dietary supplement, dental X-ray, a mouthwash, a toothpaste, acne or wound treatment product, skin scrub, and skin defoliate agent.

17 Claims, 3 Drawing Sheets

METHODS OF MAKING SILVER NANOPARTICLES AND THEIR APPLICATIONS

CROSS-REFERENCE TO RELATED APPLICATIONS

This application is a Continuation of U.S. patent application Ser. No. 16/121,310, filed on Sep. 4, 2018, which is a Continuation of U.S. patent application Ser. No. 14/432,408, filed on Mar. 30, 2015 (now U.S. Pat. No. 10,064,793, issued Sep. 4, 2018), which is a National Stage Entry of International Patent Application No. PCT/US2013/062719, filed on Sep. 30, 2013, which claims the benefit of priority under 35 U.S.C. § 119(e) from U.S. Provisional Patent Application No. 61/744,542, filed Sep. 28, 2012, all contents of which are incorporated herein by reference in their entireties.

BACKGROUND

Silver can be a potential antimicrobial agent. Silver has been known to possess strong antimicrobial properties. Silver ions such as silver nitrate and sulfadiazine had been used for the treatment of burns, wounds and several bacterial infections. Their use was largely discontinued in the 1940s, due to the development of modern antibiotics and side effects due to the presence of ionic silver.

Silver nanoparticles have unique optical and electrical properties. Colloidal silver is one of the mostly used substrates for Surface Enhanced Raman Spectroscopy (SERS) for single molecule detection. The highly reflective silver nanoparticles have also been used in metal film plasmonic solar cells to improve the conversion efficiency from photos to electrons. The capability of making highly conductive traces and films at low temperatures is of enormous commercial interest to the electronics industry.

Silver nanoparticles can be produced by various processes such as chemical reduction of silver salts in an aqueous and organic solution, radiation assisted-chemical and photoreduction in reverse micelles, thermal decomposition of silver compounds, evaporation and condensation of silver metal, etc.

The chemical reduction methods are based on reduction of silver salt with a number of reducing agents including sodium citrate, sodium borohydride, hydroxylamine hydrochloride, hydrazine, and ethylenediaminetetraacetic acid (EDTA), ascorbic acid, polyol, etc. A stabilizing agent needs to be added to the reaction mixture to prevent the aggregation of the silver nanoparticles formed unless the reducing agent itself is a stabilizing agent (such as citrate).

SUMMARY

Disclosed herein is a method of making silver nanoparticles, comprising: mixing a silver salt and a reducing agent with Formula I; wherein the reducing agent reduces the silver salt.

According to an embodiment, R is selected from a group consisting of H, OH, $CH_3$, COOH, $CONH_2$, a chemical species of Formula II, Formula III, or Formula IV, where n is a positive integer.

According to an embodiment, the silver salt is $AgNO_3$.

According to an embodiment, a molar ration of the reducing agent to silver ion is above 0.5.

According to an embodiment, the method further comprises mixing a stabilizing agent, wherein the stabilizing agent stabilizes the silver nanoparticles against aggregation.

According to an embodiment, maintaining the silver salt and the reducing agent at a temperature below 50° C.

Discloses herein is a method of making silver nanoparticles, comprising: mixing a silver salt and a reducing agent with Formula V, Formula VI, or Formula VII; wherein the reducing agent reduces the silver salt.

According to an embodiment, maintaining the silver salt and the reducing agent at a temperature above 90° C.

Disclosed herein is a method of making hydrogel particles containing silver nanoparticles, the method comprising: preparing an emulsion with a water phase and an oil phase, the water phase comprising silver nanoparticles and polysaccharide; forming hydrogel particles from the water phase by lowering a temperature of the emulsion while stirring.

According to an embodiment, the method further comprises dehydrating the hydrogel particles.

Disclosed herein is a micro particle with a diameter of 10-100 microns, wherein the micro particle is coated with silver nanoparticles.

According to an embodiment, the micro particle comprises calcium carbonate or dicalcium phosphate dihydrate.

Disclosed herein is a silver nanoparticle, wherein the silver nanoparticle is coated by polysaccharide.

Disclosed herein is a method of making polysaccharide coated silver nanoparticles, the method comprising: obtaining a solution containing the silver nanoparticles suspended therein and a stabilizing agent; replacing the stabilizing agent with polysaccharide.

Disclosed herein is a treatment product for acne or wound, comprising the silver nanoparticles coated by polysaccharide.

Disclosed herein is a method of treating acnes, comprising applying the silver nanoparticles coated by polysaccharide to the acnes.

Disclosed herein is a treatment product for acne, comprising the micro particles coated with silver nanoparticles.

DETAILED DESCRIPTION

Various reducing agents may be used to make silver nanoparticles by reducing silver salt. Examples of the reducing agents include sodium citrate, sodium borohydride ($NaBH_4$), hydroxylamine ($NH_2OH$), ascorbic acid, hydrazine ($N_2H_4$), and ethylene glycol. Most of these reducing agents, with exception of sodium citrate, do not stabilize silver nanoparticles. Namely, silver nanoparticles tend to aggregate. A stabilizing agent may be used to stabilize silver nanoparticles (i.e., reduce or prevent aggregation).

Although citrate is both a reducing agent and a stabilizing agent, it tends to yield silver nanoparticles too big in size (e.g., 40-70 nm diameter).

Others of the reducing agents may be too reactive and cause difficulties in controlling the reduction reaction. Some of the reducing agents yield toxic by-products. For example, hydroxylamine ($NH_2OH$) generates NO; citrate generates formaldehyde. NO and Formaldehyde are gaseous, and can be harmful if inhaled.

Lowering the redox potential of a reducing agent for the reduction of silver salt tends to yield more nuclei and thus smaller particle size. According to an embodiment, controlling the redox potential of a reducing agent allows control of mean size of the silver nanoparticles under easy-to-control reaction conditions (e.g., aqueous solution, 0-100° C., one atmosphere pressure), without toxic by-product or with easily removable by-product. The reducing agent may also have chemical functions that will be attached to the silver nanoparticles and thus allow various applications such as topical use for wound healing, acne treatment, fungal treatment, dental washing, x-ray agents, appliance surface desanitization, etc.

According to an embodiment, a reducing agent is an ascorbic acid derivative of

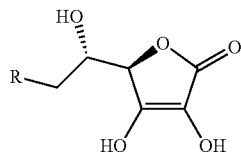

(Formula I), where R=H, OH, $CH_3$, COOH or $CONH_2$. Alternatively, R may be

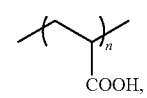

(Formula II)

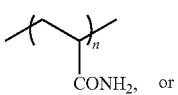

(Formula III)

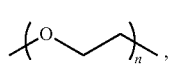

(Formula IV)

where n is a positive integer.

Figure 1:
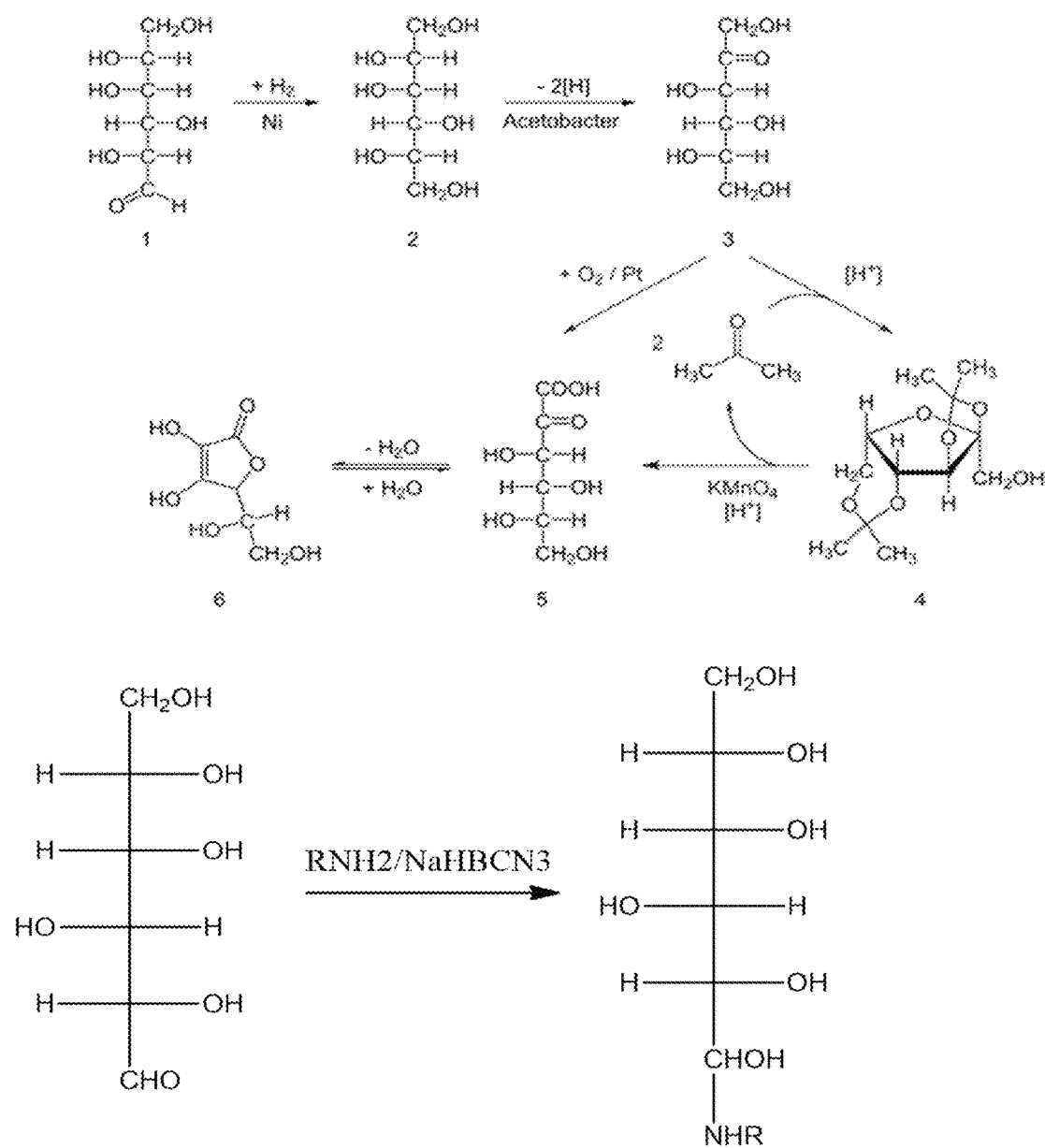
FIG. 1 shows an exemplary synthesis route of the reducing agents of Formula I.

FIG. 1 shows an exemplary synthesis route of the reducing agents of Formula I.

According to an embodiment, a method of making silver nanoparticles using a reducing agent of Formula I includes mixing a silver salt such as $AgNO_3$ and the reducing agent. In an embodiment, the concentration of the silver salt after mixing is from $1\times10^{-4}$ to $1\times10^{-2}$ mol/L. A reducing agent of Formula I may undergo different stages of oxidation. During the first stage, one mole of the reducing agent reduces 2 moles of the silver salt. In an embodiment, the molar ratio of the reducing agent to silver ion is above 0.5, which reduces or essentially eliminates free silver ions in the reaction products.

When R is a polymer (e.g., a polymer of Formulae II, III or IV), the silver nanoparticle is stabilized against aggregation. When R is a small functional group (e.g., H, OH, $CH_3$, COOH or $CONH_2$), a stabilizing agent such as citric acid, polyacrylic acid (PAA), polyvinylpyrrolidone (PVP), poly (galacturonic acid) (PGUA), alginic acid may be mixed with the silver salt and the reducing agent.

Temperature of the mix may be used to control the reaction rate (higher temperature leads to higher reaction rate) and thereby to control the size of the silver nanoparticles. Preferably, the temperature is from 0 to 100° C. at 1 atm. Preferably, the temperature is below 50° C.

The reaction usually completes within several minutes to about an hour, depending on the temperature and reagent concentration.

According to an embodiment, a reducing agent is an alpha-hydroxyl carboxylic acid derivative of

(Formula V)

(Formula VI)

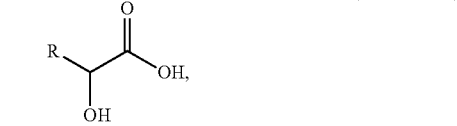

(Formula VII)

where R, $R_1$, $R_2$ may be H, OH, $CH_3$, COOH, $CONH_2$, the species of Formulae II, III, or IV.

Figure 2:
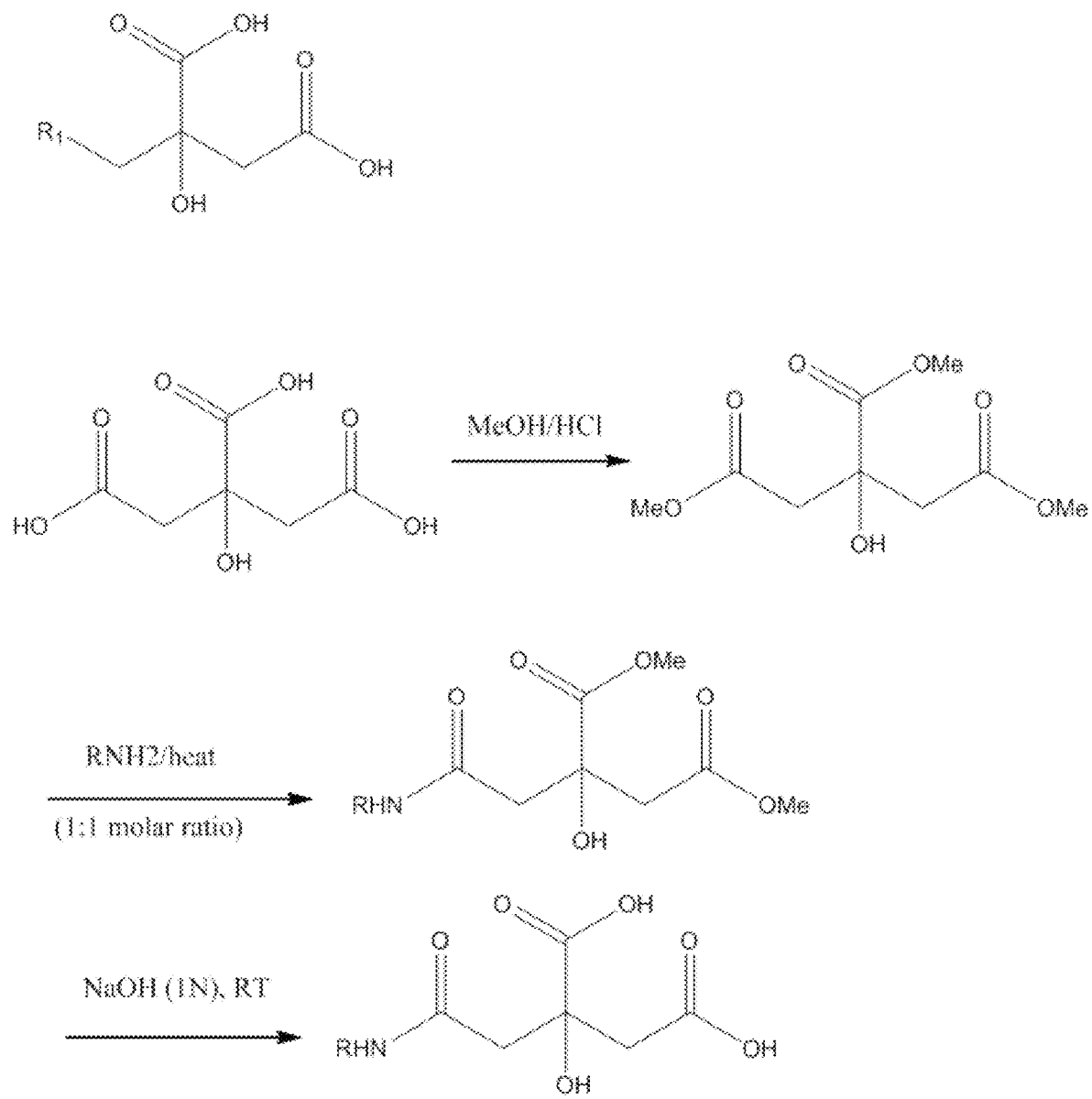
FIG. 2 shows an exemplary synthesis route of the reducing agents of Formula V.

FIG. 2 shows an exemplary synthesis route of the reducing agents of Formula V.

According to an embodiment, a method of making silver nanoparticles using a reducing agent of Formula V, VI or VII includes mixing a silver salt such as $AgNO_3$ and the reducing agent in a solution.

The silver salt and the reducing agent may be mixed in any suitable methods such as (1) heating a solution of one agent (either silver salt, or the reducing agent) to a given temperature, then adding the other agent; (2) heating a solvent (e.g., water) to a given temperatures, and adding the silver salt and the reducing agent simultaneously with agitation; or (3) mixing the silver salt and the reducing agent into a solvent at room temperature, heating the solution to a given temperature to cause nucleation.

Preferably, the solution is heated to the boiling point of water. For some reducing agents such as citrate, the reaction rate at room temperature (about 25° C.) is very slow. At room temperature, it can take many days to observe any nanoparticles due to slow nucleation, which leads to large size and large dispersion in size of the silver nanoparticles. At higher temperature, the reaction is faster. At 100° C., nucleation occurs within about 2 minutes.

Preferably, the solution is kept at an elevated temperature for 15-60 minutes to allow the reaction to complete.

Silver nanoparticles may be collected by centrifugation. Undesirable by-products may be washed away. Silver nanoparticles may be resuspended in a suitable medium.

According to an embodiment, silver nanoparticles prepared using the reducing agent of Formula I, V, VI or VII have a relatively narrow size distribution (e.g., <±20%). The diameter of the silver nanoparticles may be controlled to be less than 50 nm. The silver nanoparticle suspension may have less than 1% free silver ions. The silver nanoparticle suspension may be essentially free of free silver ions. The silver nanoparticles may be suspended in an aqueous solution and have a shelf life of more than six months. Preferably, the silver nanoparticles are suspended in a solution with a stabilizing agent (e.g., citrate).

Figure 3:
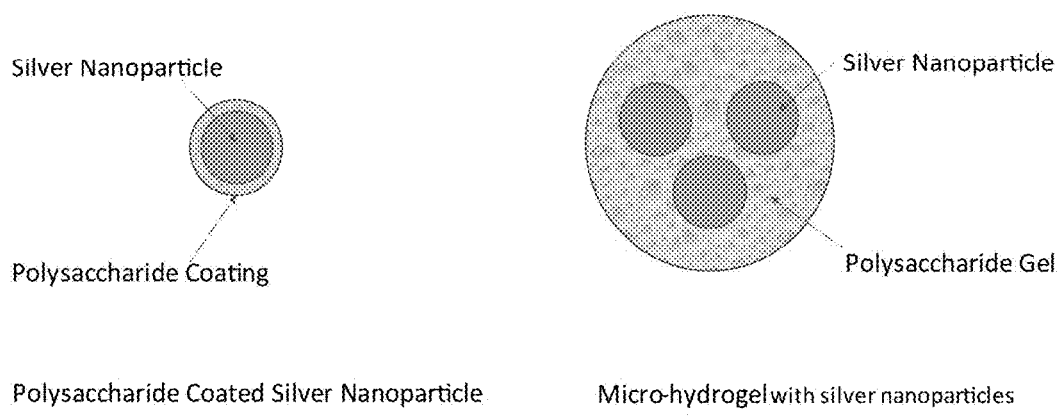
FIG. 3 shows a silver nanoparticle with polysaccharide coating and silver nanoparticles embedded in polysaccharide micro-hydrogel.

According to an embodiment, as schematically shown in FIG. 3, silver nanoparticles may be coated with polysaccharide. Polysaccharide coating is digestible by bacteria and exposed silver nanoparticles may kill the bacteria. Polysaccharide coated silver nanoparticles may be suitable as food supplement.

According to an embodiment, a method of making hydrogel particles containing silver nanoparticles includes:
preparing an water-in-oil emulsion at a temperature higher than room temperature, the water phase containing the silver nanoparticles and polysaccharide which can form gel when the temperature is lowed (example agar agar);
forming hydrogel particles from the water phase by lowering the temperature of the emulsion while stirring;
collecting hydrogel particles;
washing the oil phase away.

The hydrogel particles contain the silver particles. The hydrogel particles may be collected by centrifugation. The hydrogel particles may be dehydrated by adding ethanol. According to an embodiment, dehydrated hydrogel particles may be used in wound dressing. Dehydrated hydrogel particles have a dual function: reducing fluid near wound and killing bacteria.

According to an embodiment, silver nanoparticles may be used in a skin scrub/defoliate agent. Silver nanoparticles may be coated (e.g., 90% area coverage) on micro particles (e.g., calcium carbonate or dicalcium phosphate dihydrate particles of 10-100 microns diameter). The micro particles may be formed using any suitable method such as precipitation. The micro particles may be coated with silver nanoparticles in an acidic solution because the micro particles may have a positive charge and the silver nanoparticles may have a negative charge. The skin scrub/defoliate agent may further contain soap. The skin scrub/defoliate agent may be used to treat acnes.

According to an embodiment, an acne/wound treatment product includes silver nanoparticles coated with polysaccharide (preferably short chain polysaccharide).

According to an embodiment, silver nanoparticles coated with polysaccharide may be prepared using a method including: obtaining a solution containing the silver nanoparticles suspended therein and a stabilizing agent (such as citric acid and small molecules); replacing the stabilizing agent with a relatively large polysaccharide chains (e.g., at a concentration from 1 to 10 ppm).

According to an embodiment, silver nanoparticles coated with polysaccharide may be prepared using a method including: preparing silver nanoparticles using a reducing agent with a polysaccharide chain.

According to an embodiment, the acne treatment product may be applied directly to acnes or other wounds.

As an example, polysaccharide may be polygalacturonic acid (PGUA).

According to an embodiment, an acne/wound treatment product includes silver nanoparticles at a concentration of at least $10^9$ particles/ml, and the acne/wound treatment product is essentially free of silver ions.

According to an embodiment, an acne/wound treatment product includes 20-42% water and about 50% micro particles coated with silver nanoparticles.

The silver nanoparticles may have other applications such as tooth paste and mouthwash solution containing 10-100 ppm silver nanoparticles as antibacterial agent and optional 0.1-0.5% sodium fluoride (NaF) as dental cavity inhibitor.

According to an embodiment, a wound dressing includes fabric with silver nanoparticles embedded therein.

According to an embodiment, a method of making a wound dressing includes obtaining a fabric with positive charge; soaking the fabric in a suspension of silver nanoparticles; washing the fabric with water (preferably deionized water); drying the fabric. The wound dressing may be applied directly to a wound.

According to an embodiment, a bandage includes a non-adhesive absorbent pad with polysaccharide coated silver nanoparticles embedded therein.

According to an embodiment, a fungal treatment product includes: polysaccharide coated silver nanoparticles embedded in a gel; the gel also containing pentylene glycol, glycerine, aloe vera, trethanolamine, carbomer, PPG-2 isceteth-20 acetate, EDTA, methylparaben, and DMDM hydantoin.

According to an embodiment, a fungal treatment/deodorant product includes silver nanoparticles suspended in a citrate solution. The fungal treatment/deodorant product may also include methanol and/or DMSO.

According to an embodiment, a toothpaste includes 10-20 ppm or 10-100 ppm of silver nanoparticles. The toothpaste may also include an abrasive such as dicalcium phosphate dehydrate, silicon dioxide and/or calcium carbonate. The toothpaste may also include sodium fluoride, sorbitol, Xanthan Gum, Stevia, flavour or a combination thereof.

According to an embodiment, a toothpick or a floss product may be coated with silver nanoparticles.

According to an embodiment, a mouthwash includes at least 10 ppm silver nanoparticles. The mouthwash may further include NaF, pyrophosphate, hydrogen peroxide, methanol, sorbitol, sucralose, sodium saccharin, xylitol, citric acid, benzoic acid, or a combination thereof.

According to an embodiment, using the mouthwash before dental X-ray may help identification of dental cavities.

According to an embodiment, a dietary supplement may include silver nanoparticles.

While specific embodiments of the invention have been described above, it will be appreciated that the invention may be practiced otherwise than as described. The descriptions above are intended to be illustrative, not limiting. Thus it will be apparent to one skilled in the art that modifications may be made to the invention as described without departing from the scope of the appended claims.

What is claimed is:

1. A method of making a product comprising a hydrogel particle comprising:
preparing an emulsion with a water phase and an oil phase, the water phase comprising a silver nanoparticle and a polysaccharide;
forming the hydrogel particles from the water phase by lowering a temperature of the emulsion while stirring, and wherein the silver nanoparticle has a diameter less than 50 nm with a size distribution of <±20%.

2. The method of claim 1, further comprising dehydrating the hydrogel particles.

3. The method of claim 2, wherein the polysaccharide coats the silver nanoparticle to form a coated silver nanoparticle.

4. The method of claim 3, wherein the coated silver nanoparticle is embedded within the hydrogel particle, wherein the hydrogel particle has a size between about 10 microns to about 100 microns.

5. The method of claim 1, wherein the polysaccharide is digestible by bacteria.

6. The method of claim 5, wherein the polysaccharide is polygalacturonic acid (PGUA).

7. The method of claim 1, wherein the silver nanoparticle has a shelf life more than six months.

8. The method of claim 1, the method further comprising:

mixing a micro particle, a silver salt and a reducing agent with a formula:

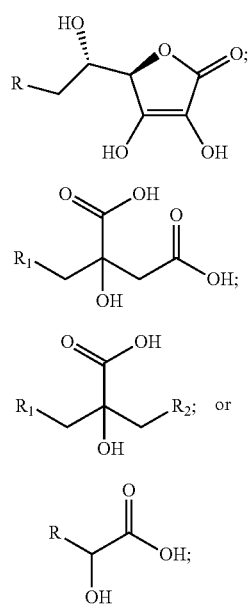

(Formula I)

(Formula V)

(Formula VI) or (Formula VII)

wherein the reducing agent reduces the silver salt to form the silver nanoparticles with the size distribution of $<\pm20\%$; and coating a surface area of the micro particle with the silver nanoparticle;

wherein $R_1$ and $R_2$ is H, OH, $CH_3$, COOH or $CONH_2$ and wherein R is selected from a group consisting of H, OH, $CH_3$, COOH, $CONH_2$, a chemical species of (Formula II)

(Formula III)

(Formula IV)

where n is a positive integer.

9. The method of claim 1, wherein the emulsion has less than 1% of free silver ions.

10. The method of claim 8, wherein the silver nanoparticles has a shelf life more than six months.

11. The method of claim 10, wherein the silver salt is $AgNO_3$.

12. The method of claim 10, wherein a molar ration of the reducing agent to silver ion is above 0.5.

13. The method of claim 10, further comprising mixing a stabilizing agent, wherein the stabilizing agent stabilizes the silver nanoparticle against aggregation.

14. The method of claim 10, wherein the silver salt and the reducing agent are maintained and mixed at a temperature below 50° C.

15. The method of claim 10, wherein the mixing and the coating are in the sequential order.

16. The method of claim 10, wherein the silver nanoparticle has a diameter of less than 50 nm.

17. The method of claim 10, further comprising a microparticle, wherein a surface area of the microparticle is coated with the silver nanoparticle embedded within a polysaccharide.

* * * * *